US012779196B2

(12) United States Patent
Feith et al.

(10) Patent No.: US 12,779,196 B2
(45) **Date of Patent: *Nov. 3, 2026**

(54) FORCE-CONTROLLED RELEASE CONNECTOR WITH INTEGRATED SAFETY FEATURES

(71) Applicant: Becton, Dickinson and Company, Franklin Lakes, NJ (US)

(72) Inventors: Raymond P. Feith, Chino Hills, CA (US); Jason Andrew Wine, Brea, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/925,928

(22) Filed: Oct. 24, 2024

(65) Prior Publication Data

US 2025/0050090 A1 Feb. 13, 2025

Related U.S. Application Data

(63) Continuation of application No. 17/986,395, filed on Nov. 14, 2022, now Pat. No. 12,151,078.

(51) Int. Cl.
*A61M 39/26* (2006.01)
*A61M 39/10* (2006.01)
(Continued)

(52) U.S. Cl.
CPC ............ *A61M 39/26* (2013.01); *A61M 39/10* (2013.01); *A61M 2039/1061* (2013.01);
(Continued)

(58) Field of Classification Search
CPC ............ A61M 39/26; A61M 2039/261; A61M 2039/262; A61M 2039/263;
(Continued)

(56) References Cited

U.S. PATENT DOCUMENTS 5,259,843 A * 11/1993 Watanabe ............. A61M 39/00 604/905
5,492,147 A * 2/1996 Challender ............. F16L 37/28 604/905

(Continued)

FOREIGN PATENT DOCUMENTS

WO WO-2019171371 A1 * 9/2019 ............ A61M 39/26
WO 2022149339 A1 7/2022

OTHER PUBLICATIONS

MERIT FastBreak Breakaway Connector Brochure, https://www.merit.com/peripheral-intervention/drainage/accessories/fastbreak-breakaway-connector/.

*Primary Examiner* — David Colon-Morales
(74) *Attorney, Agent, or Firm* — The Webb Law Firm

(57) ABSTRACT

A connector includes an outer housing defining a lumen, a first male coupler mateable with a needle-free valve and positioned at a first end of the outer housing, a second male coupler positioned at a second end of the outer housing, a valve system to control fluid flow through the lumen, and an actuator movable within the outer housing between a first position and a second position. A pinch clamp of the connector operates to selectively deflect locking fingers of the actuator from a locked position to a movement position to selectively enable or prevent movement of the actuator from the first position to the second position. The actuator, based on its positioning in the first or second position, causes the valve system to be in a closed state or an open state and blocks or allows the first coupler to couple with the needle-free valve.

14 Claims, 8 Drawing Sheets

(51) Int. Cl.
*A61M 39/28* (2006.01)
*F16L 37/35* (2006.01)

(52) U.S. Cl.
CPC . *A61M 2039/267* (2013.01); *A61M 2039/268* (2013.01); *A61M 39/28* (2013.01); *F16L 37/35* (2013.01)

(58) Field of Classification Search
CPC ...... A61M 2039/267; A61M 2039/268; A61M 39/10; A61M 2039/1061; F16L 55/1015; F16L 37/35
See application file for complete search history.

(56) References Cited

U.S. PATENT DOCUMENTS

| | | | | | |
|---|---|---|---|---|---|
| 5,676,346 | A * | 10/1997 | Leinsing | A61M 39/26 | 604/905 |
| 5,820,614 | A * | 10/1998 | Erskine | F16L 55/1007 | 604/905 |
| 6,706,022 | B1 * | 3/2004 | Leinsing | A61M 39/26 | 604/247 |
| 6,964,406 | B2 * | 11/2005 | Doyle | F16L 29/04 | 251/149.6 |
| 7,396,051 | B2 * | 7/2008 | Baldwin | A61M 39/26 | 604/905 |
| 7,559,530 | B2 * | 7/2009 | Korogi | A61B 5/154 | 251/149.6 |
| 7,645,274 | B2 * | 1/2010 | Whitley | A61M 39/26 | 604/537 |
| 7,803,140 | B2 * | 9/2010 | Fangrow, Jr. | A61M 39/26 | 604/256 |
| 7,998,134 | B2 * | 8/2011 | Fangrow | A61M 39/14 | 604/535 |
| 8,277,424 | B2 * | 10/2012 | Pan | A61M 39/26 | 604/249 |
| 8,647,310 | B2 * | 2/2014 | Fangrow, Jr. | A61M 39/26 | 604/236 |
| 9,138,572 | B2 * | 9/2015 | Zeytoonian | A61M 39/26 | |
| 9,345,828 | B2 * | 5/2016 | Browne | A61M 5/162 | |
| 9,849,277 | B2 * | 12/2017 | Stroup | A61M 39/22 | |
| 9,855,412 | B2 * | 1/2018 | Chen | A61M 39/26 | |
| 9,861,805 | B2 * | 1/2018 | Dennis | A61M 39/26 | |
| 9,933,094 | B2 * | 4/2018 | Fangrow | F16L 29/00 | |
| 10,478,606 | B2 * | 11/2019 | Yang | A61M 39/24 | |
| 10,518,078 | B2 * | 12/2019 | Stjernberg Bejhed | F16L 29/005 | |
| 10,655,768 | B2 * | 5/2020 | Jones | A61M 39/24 | |
| 10,806,666 | B2 * | 10/2020 | Chih | A61J 1/2096 | |
| 10,864,362 | B2 * | 12/2020 | Jones | A61M 39/1011 | |
| 11,065,433 | B2 * | 7/2021 | Faden | A61M 5/14216 | |
| 11,207,514 | B2 * | 12/2021 | Kakinoki | A61M 39/10 | |
| 11,491,084 | B2 * | 11/2022 | Ueda | A61M 39/14 | |
| 11,491,317 | B2 * | 11/2022 | Pütter | A61M 39/10 | |
| 11,504,517 | B2 * | 11/2022 | Call | A61M 39/1011 | |
| 11,708,924 | B2 * | 7/2023 | Mansour | A61M 39/10 | 251/149 |
| 12,151,078 | B2 * | 11/2024 | Feith | A61M 39/10 | |
| 2005/0087715 | A1 * | 4/2005 | Doyle | A61M 39/26 | 604/537 |
| 2014/0296794 | A1 | 10/2014 | Li | | |
| 2018/0140819 | A1 | 5/2018 | Yang | | |
| 2019/0184152 | A1 | 6/2019 | Kakinoki | | |
| 2021/0220633 | A1 | 7/2021 | Feith et al. | | |
| 2023/0355946 | A1 | 11/2023 | Kuriyama | | |

* cited by examiner

FORCE-CONTROLLED RELEASE CONNECTOR WITH INTEGRATED SAFETY FEATURES

CROSS-REFERENCE TO RELATED APPLICATIONS

This application is a continuation of U.S. patent application Ser. No. 17/986,395, filed Nov. 14, 2022, entitled "Force-Controlled Release Connector with Integrated Safety Features", the disclosure of which is incorporated herein in its entirety.

BACKGROUND OF THE INVENTION

Field of the Invention

The present disclosure relates to a force controlled release connector for use with needle-free valves, with safety features integrated therein.

Description of Related Art

Catheters are commonly used to administer fluids into and out of the body. Patients in a variety of settings, including in hospitals and in home care, receive fluids, pharmaceuticals, and blood products via a vascular access device (VAD) that includes such a catheter inserted into a patient's vascular system. A common VAD includes a plastic catheter that is inserted into a patient's vein, with a length of the catheter varying from a few centimeters when the VAD is a peripheral intravenous catheter (PIVC) to many centimeters when the VAD is a central venous catheter (CVC), as examples. A VAD may be indwelling for short term (days), moderate term (weeks), or long term (months to years).

In some instances, the VAD is part of a larger catheter system, where tubing or an intravenous line extends out from an adapter or connector of the VAD to provide additional flexibility for medical professionals in terms of administering and/or withdrawing fluids from the VAD. The tubing may be part of an extension set that is integrated with the VAD (an integrated catheter system) or provided separate from the VAD (a non-integrated catheter system), according to various embodiments.

During use of catheter systems as described above, it is possible for the catheter to become dislodged. That is, while securement devices are used to attach the VAD and/or associated tubing to the skin of a patient, catheter dislodgement may occur when greater forces are exerted upon the catheter than the securement device was designed to withstand. Examples of such forces include patients rolling over in bed or catching their lines on bed rails, moving patients to a different bed, fidgeting by pediatric patients, or disoriented adult patients' pulling out their IV lines.

Accordingly, a need exists in the art for improved connection devices that provide a controlled disconnection to prevent a transfer of force to the VAD that may lead to catheter dislodgement in patients. A further need exists for such connection devices to include safety features integrated therein that prevent unauthorized reattachment of components to the connection device and prevent fluid leakage upon a disconnection from the connection device.

SUMMARY OF THE INVENTION

Provided herein is a force controlled release connector coupleable to a needle-free valve. The connector includes an outer housing having a first end and a second end, the outer housing defining a lumen extending between the first end and the second end. The connector also includes a first coupler positioned at the first end of the outer housing, the first coupler being a first male connection mateable with a female connection of the needle-free valve and being separable from the needle-free valve when a pre-determined pulling force is applied between the first male connection and the needle-free valve. The connector further includes a second coupler positioned at the second end of the outer housing, a valve system positioned within the outer housing to control fluid flow through the lumen, and an actuator movable within the outer housing in a lengthwise direction between a first position and a second position, the actuator including an arrangement of locking fingers configured to deflect from a locked position to a movement position. The connector still further includes a pinch clamp engageable with the locking fingers to deflect the locking fingers from the locked position to the movement position, with movement of the actuator from the first position to the second position enabled with the locking fingers in the movement position and prevented with the locking fingers in the locked position. When in the first position, the actuator causes the valve system to be in a closed state that seals the lumen from an external environment and blocks the first coupler from coupling with the needle-free valve. When in the second position, the actuator causes the valve system to be in an open state that opens the lumen to the external environment and allows the first coupler to couple with the needle-free valve and coupling.

In some embodiments, the first male connection includes an extension tip and a collar portion positioned about at least a portion of the extension tip, the collar portion having an arrangement of flexible fingers configured to selectively disengage the connector from the needle-free valve when the pre-determined pulling force is applied.

In some embodiments, the actuator includes a base and a first protrusion extending outwardly from the base toward the first end of the outer housing, the first protrusion positioned within a portion of the lumen that extends through the extension tip. The actuator also includes a second protrusion extending outwardly from the base toward the second end of the outer housing and engagement arms extending outwardly from the base toward the first end of the outer housing and positioned partially about the extension tip and to engage the needle-free valve, with the locking fingers extending outwardly from the base toward the second end of the outer housing.

In some embodiments, the valve system includes a first valve member in the form of a plug positioned on an end of the first protrusion and a second valve member retained within the housing between the second end of the housing and the base of the actuator, the second valve member including a tubular body that engages the base at a first end of the tubular body, with a split septum positioned at a second end of the tubular body.

In some embodiments, the tubular body biases the actuator in the first position, with engaging of the needle-free valve with the first coupler moving the actuator from the first position to the second position and disengaging of the needle-free valve from the first coupler returning the actuator to the first position.

In some embodiments, with the actuator in the first position, the plug blocks a first end opening of the lumen positioned at an end of the extension tip, and the second protrusion is spaced apart from the split septum and the split septum is in a closed position, such that the first valve member and the second valve member seal the lumen from the external environment.

In some embodiments, with the actuator in the second position, the plug is spaced apart from the first end opening of the lumen positioned at the end of the extension tip, and the second protrusion contacts and engages the split septum to force the split septum into an open position, such that the first valve member and the second valve member open the lumen to the external environment.

In some embodiments, the second protrusion includes a pair of protrusion fingers spaced apart to make contact on opposing sides of a slit in the split septum.

In some embodiments, with the actuator in the first position and the locking fingers in the locked position, the engagement arms of the actuator prevent the female connection of the needle-free valve from threadingly engaging the collar portion of the first male connection.

In some embodiments, the outer housing includes a ledge extending radially inward from an inner surface of the housing, with the locking fingers engaging the ledge when in the locked position, to prevent movement of the actuator from the first position to the second position, and disengaging from the ledge when in the movement position, to enable movement of the actuator from the first position to the second position.

In some embodiments, the pinch clamp is a pinch collar positioned about the outer housing and within a seat formed in the outer housing, adjacent the ledge, the seat including openings formed therein through which protrusions of the pinch collar engage the locking fingers, to enable deflection of the locking finger from the locked position to the movement position.

In some embodiments, the outer housing includes a pair of channels formed on an outer surface thereof, each of the pair of channels extending between the seat and the first end of the outer housing, and wherein the protrusions on the pinch collar are positioned to slide within the pair of channels, to enable removal of the pinch collar from the outer housing.

In some embodiments, the second coupler is a second male connection including another extension tip and another collar portion, the second male connection mateable with a female connection of another needle-free valve.

In some embodiments, the outer housing includes a first housing portion and a second housing portion, wherein the first housing portion comprises the first coupler and the second housing portion comprises the second coupler.

Also provided herein is a catheter system that includes a catheter having a catheter distal end and a catheter proximal end and a catheter adapter coupled to the catheter proximal end and including a lumen in fluid communication with the catheter, the catheter adapter including a side port in fluid communication with the lumen. The catheter system also includes extension tubing in fluid communication with the side port of the catheter adapter, the extension tubing having a proximal access port coupled to a proximal end portion thereof. A connector as previously described is further provided in the catheter system, with the second coupler of the connector coupled to the proximal access port.

In some embodiments, the catheter system includes an intravenous (IV) fluid system comprising an IV bag having IV fluid therein and IV tubing extending out from the IV bag and a needle-free valve coupled to an end of the IV tubing opposite the IV bag, with the needle-free valve coupled to the first male connection of the connector.

In some embodiments, the IV tubing is primed upon coupling of the needle-free valve to the first male connection and prior to coupling of the another needle-free valve to the second male connection.

In some embodiments, the arrangement of flexible fingers of the first male connection is configured to selectively disengage the connector from the needle-free valve when a pre-determined pulling force is applied to the needle-free valve, via the IV tubing.

In some embodiments, IV fluid present in the connector is sealed within the connector by the valve system, upon disconnecting of the needle-free valve from the first male connection.

In some embodiments, the proximal access port is a needle-free valve, the needle-free valve coupled to the second male connection of the second coupler.

DESCRIPTION OF THE INVENTION

Figure 1:
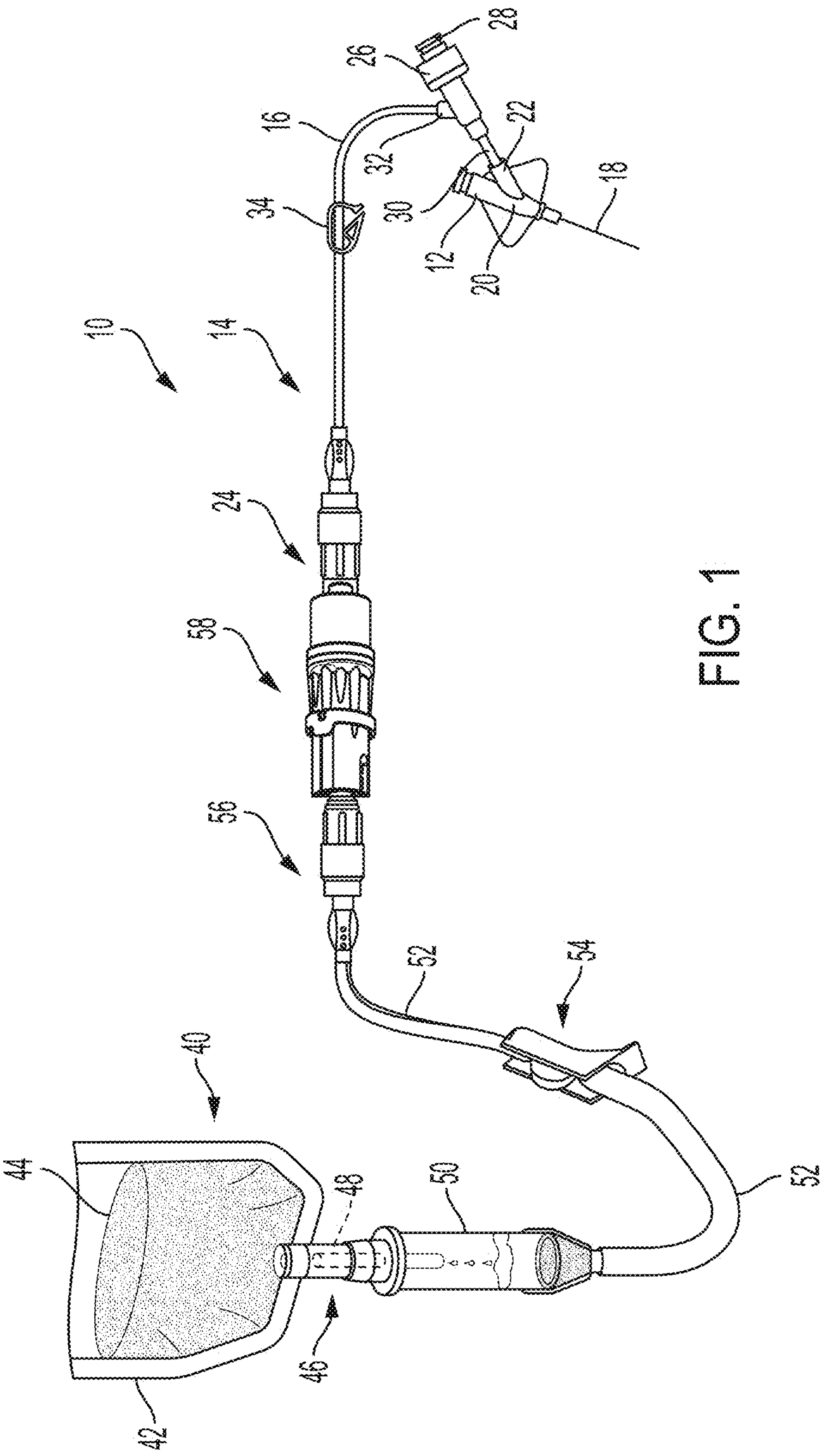
FIG. 1 is a perspective view of a catheter system in which aspects or embodiments of the present application may be implemented, according to an aspect or embodiment of the present application.
Figure 2:
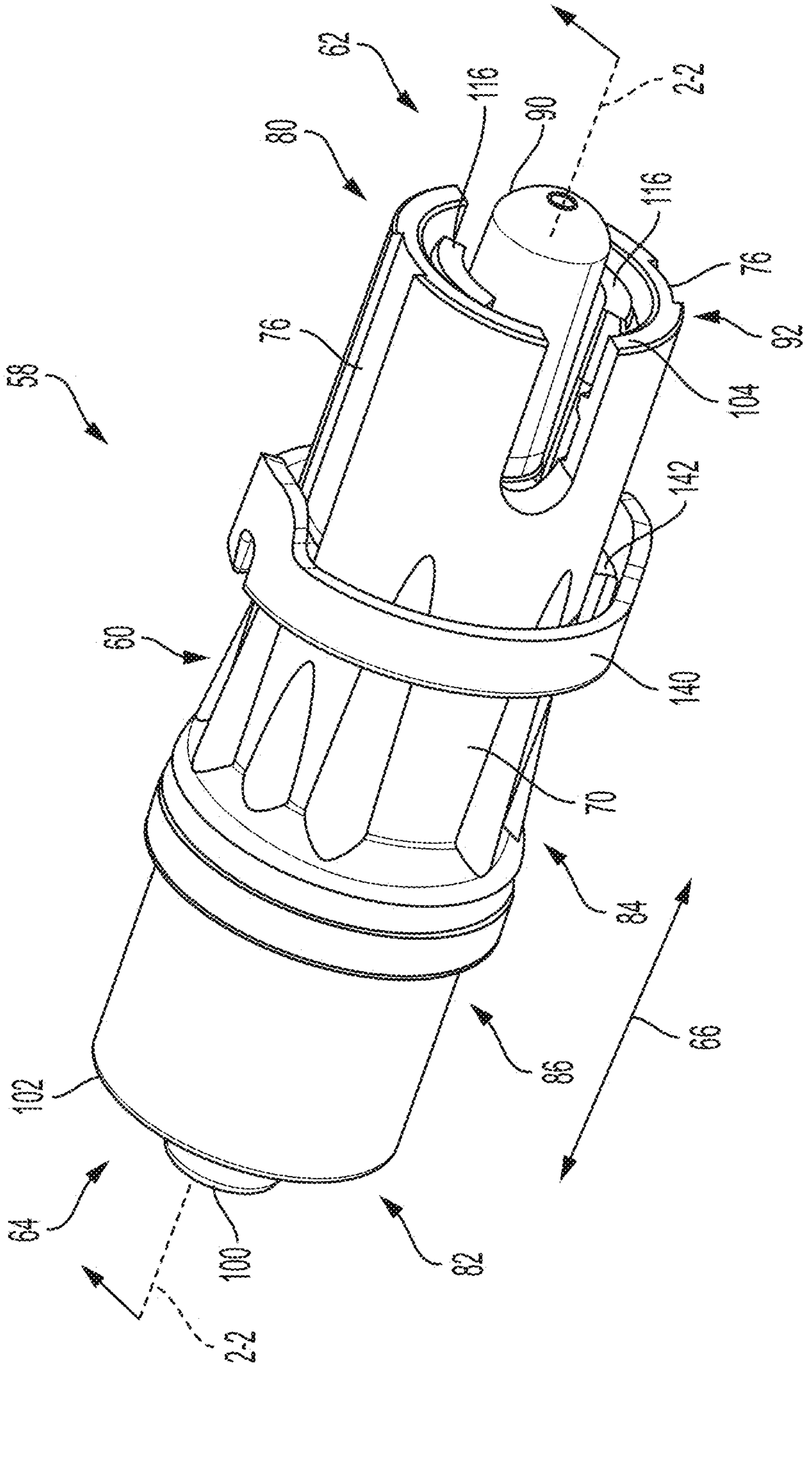
FIG. 2 is a perspective view of a force-controlled release connector, according to an aspect or embodiment of the present application.
Figure 3:
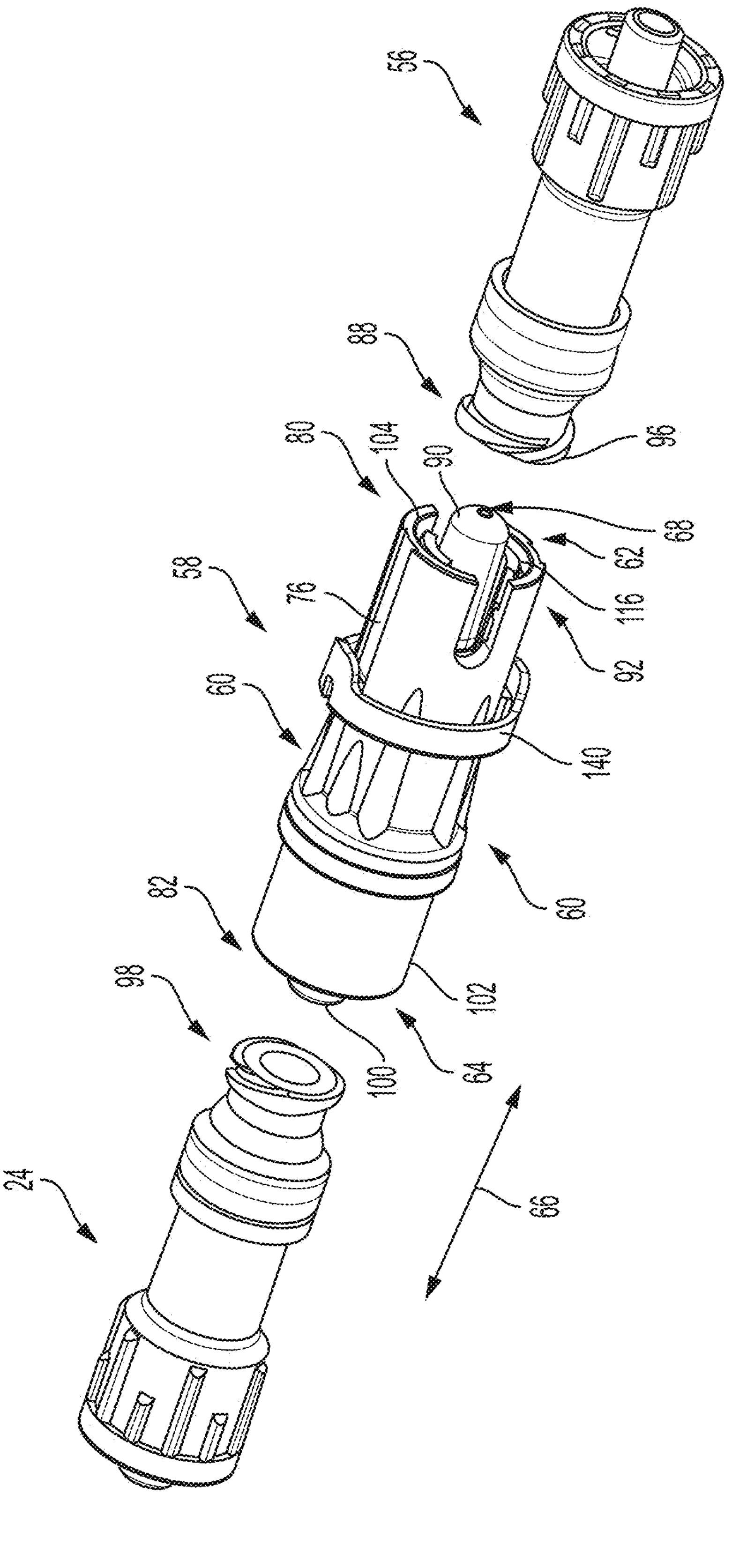
FIG. 3 is a perspective view of the force-controlled release connector of FIG. 2 relative to a pair of needle-free connectors that are coupleable thereto.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present disclosure.

For the purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

In the present disclosure, the distal end of a component or of a device means the end furthest away from the hand of the user and the proximal end means the end closest to the hand of the user, when the component or device is in the use position, i.e., when the user is holding a catheter insertion device in preparation for or during use. Similarly, in this application, the terms "in the distal direction" and "distally" mean in the direction toward the distal tip of the needle or catheter of the system, and the terms "in the proximal direction" and "proximally" mean in the direction opposite the direction of the distal tip of the needle or catheter.

Referring to FIG. 1, a catheter system 10 is shown, according to one aspect or embodiment with which embodiments of the invention may be implemented. The catheter system 10 includes a catheter adapter 12, along with an extension set 14 (including extension tubing 16) that, in some embodiments, may be integrated with the catheter adapter 12 (an "integrated extension set") or not integrated with the catheter adapter 12 (a "non-integrated extension set"). The catheter adapter 12 includes a catheter 18, a body 20 receiving the catheter 18, and a side port 22 in fluid communication with the catheter 18. The extension set 14 includes a proximal access port 24 coupled to a proximal end portion of the extension tubing 16, with the extension tubing 16 in fluid communication with the side port 22 of the catheter adapter 12. The proximal access port 24 may include a needle-free connector integrated into the proximal access port 24 or separately connected to the proximal access port 24, with the proximal access port 24 thus referred to hereafter as a "needle-free connector 24" that is configured to receive a blunt introducer of connector. More specifically, the needle-free connector 24 may be configured as a split-septum needle-free connector such as, for example a SmartSite™ needle-free connector from Becton, Dickinson and Co., or any other appropriate split-septum needle-free connector.

In some aspects or embodiments, the system 10 may include a near patient access port 26 in fluid communication with the side port 22 of the catheter adapter 12, with the near patient access port 26 including a connector portion 28 configured to be coupled to a peripheral probe device. The near patient access port 26 is configured to provide catheter access to peripheral devices such as, e.g., a blood draw device (e.g., PIVO™ from Becton, Dickinson and Company), or a vascular access probe (VAP) for in-vein digital measurement of patient data such as temperature, pH, lactate, and/or other blood-based measurements. In some embodiments, the near patient access port 26 is coupled to the side port 22 of the catheter adapter 12 via a length of intermediate tubing 30. However, in other embodiments, the near patient access port 26 may be coupled directly to the side port 22, or connected via another intermediate member.

The near patient access port 26 includes the connector portion 28, which in some embodiments, is configured to be compatible with peripheral devices such as blood draw devices and/or vascular access probes. In some embodiments, the connector portion 28 is configured as a needle-free connector configured to receive a blunt introducer of a blood draw device. More specifically, the connector portion 28 may be configured as a split-septum needle-free connector with direct probe access such as, e.g., Q-Syte™ or SmartSite™ needle-free connectors from Becton, Dickinson and Co., or any other appropriate split-septum needle-free connector. Alternatively, in other embodiments, the connector portion 28 may be formed of a non-split-septum-type needle-free connector. With the near patient access port 26 fluidly coupled to the catheter adapter 12 via the side port 22, the system 10 provides for probe (or tube) access from a peripheral probe device through the indwelling catheter 18. The near patient access port 26 further includes a secondary port 32 positioned near a distal end thereof. In some embodiments, the secondary port 32 is coupled to the extension tubing 16 of integrated extension set 14. A clamp 34 may be provided on the integrated extension set 14, with the clamp 34 configured to selectively restrict flow through the extension tubing 16 of integrated extension set 14.

In other aspects or embodiments, extension tubing 16 of the extension set 14 may extend directly from the side port 22 of the catheter, with the system 10 not including the near patient access port 26. In such embodiments, the system 10 may incorporate the BD Nexiva™ closed peripheral IV catheter system or the BD Nexiva™ Diffusics™ closed IV catheter system, as non-limiting examples.

As shown in FIG. 1, the catheter system 10 may further include an IV fluid system 40 that can be put in fluid communication with the extension set 14 to deliver an IV fluid to a patient. The IV fluid system 40 includes an IV bag 42 that provides a source of IV fluid 44. A connector 46 is provided for connection to the IV bag 42, with the connector 46 including a spike 48 or another type of connection known by those of skill in the art. A drip chamber 50 is coupled to connector 46 that functions as a metering device to control a flow rate of IV fluid 44 provided from the IV bag 42 to the extension set 14, with IV tubing 52 extending from the drip chamber 50 that provides a conduit to convey IV fluid 44 from the drip chamber 50 and the IV bag 42 to the extension set 14. In some embodiments, a clamp 54 may be attached to the IV tubing 52 that permits the flow of IV fluid 44 exiting the drip chamber 50 to be controlled and stopped.

For placing the IV fluid system 40 in fluid communication with the extension set 14, an arrangement of ports and/or connectors is provided for coupling the IV fluid system 40 to the needle-free connector 24 of extension set 14. In some embodiments, an arrangement of an IV access port 56 and a force controlled release connector 58 is provided for connecting the IV fluid system 40 to extension set 14 (i.e., to needle-free connector 24 of the extension set 14).

The IV access port 56 is provided at an end of IV tubing 52 opposite from the IV bag 42 and drip chamber 50 to provide a means for connecting to the IV fluid system 40. The IV access port 56 may include a needle-free connector integrated into the IV access port 56 or separately connected to the IV access port 56, with the IV access port 56 thus referred to hereafter as a "needle-free connector 56" that is configured to receive a blunt introducer of connector. More specifically, the needle-free connector 56 may be configured as a split-septum needle-free connector such as, for example a SmartSite™ needle-free connector from Becton, Dickinson and Co., or any other appropriate split-septum needle-free connector.

The force controlled release connector 58 is positioned between the needle-free connector 56 of IV fluid system 40 and the needle-free connector 24 of extension set 14 and is configured to provide for coupling and a fluid connection between the IV fluid system 40 and the extension set 14. The connector 58 is coupled to both the needle-free connector 56 and needle-free connector 24 and, as will be explained in further detail below, the connector 58 is configured to separate from the needle-free connector 56 when a predetermined separation force is applied to the connector 58. The connector 58 is thus configured to detach from the needle-free connector 56 to prevent excessive forces from being transmitted to the catheter adapter 12 via the extension tubing 16. For example, in the event of excessive movement of the IV bag 42 and IV tubing 52, the connector 58 will detach from the needle-free connector 56, thereby preventing a transfer of force/movement of the IV bag 42 and IV tubing 52 to the extension tubing 16 that might cause a dislodging or disrupting of the placement of the catheter 18.

Referring to FIGS. 2-8, the force controlled release connector 58 is shown in greater detail according to an embodiment of the disclosure. The force controlled release connector 58 includes an outer housing 60 that may be generally cylindrical in shape, according to some embodiments. The housing 60 extends between a first end 62 and a second end 64 in a lengthwise direction 66 and generally defines a lumen 68 in an interior thereof (see FIGS. 3-7) that extends between the first and second ends 62, 64, thereby providing a fluid path within the connector 58. A groove or seat 69 is formed in the outer housing 60 at a location between the first and second ends 62, 64, generally in a middle section of the housing 60. The seat 69 is recessed radially inward from an outer surface 70 of the housing 60 and includes one or more openings 72 (e.g., two openings) formed therein that provide access into the interior of the housing 60. Adjacent the area of seat 69, and on an inner surface 75 of housing 60, a ledge 74 is formed that extends radially inward from the inner surface 75 of the housing 60. The ledge 74 may be annular in shape, so as to extend generally about the inner surface 75 of the housing 60, or may be structured as separate ledge portions positioned at desired locations on the inner surface 75.

In some embodiments, the outer housing 60 includes channels 76 formed on the outer surface 70 thereof that extend in the lengthwise direction 66. The channels 76 extend in the lengthwise direction 66 from the seat 69 to the first end 62 of the housing 60. The channels 76 are recessed radially inward from the outer surface 70 of the housing 60 and may be formed at positions that align circumferentially with the location of openings 72 formed in the seat 69.

At each of the opposing first and second ends 62, 64 of the housing 60, a coupler is provided that provides for engagement of the connector 58 with other suitable ports or connectors, such as needle-free connectors 24, 56. A first coupler 80 is thus provided at the first end 62 of housing 60 and a second coupler 82 is provided at the second end 64 of housing 60. In some embodiments the housing 60 may be formed as a two-piece housing 60, with the first coupler 80 making up part of a first housing portion 84 and the second coupler 82 making up part of a second housing portion 86. The first and second housing portions 84, 86 may be secured together via a clip- or turn-type connection to thereby form the outer housing 60 of the connector 58.

According to embodiments of the disclosure, the first coupler 80 of connector 58 is configured as a male connection (i.e., hereafter "first male connection 80"), such as a male luer connection, configured to couple with a corresponding female luer connection of a needle-free connector coupled thereto. In the catheter system of FIG. 1, the first male connection 80 may thus connect to a female luer connection 88 of needle-free connector 56 (FIG. 3), which as stated above may be a SmartSite™ needle-free connector from Becton, Dickinson and Co. The first male connection 80 generally includes an extension tip 90 and a collar portion 92, with the collar portion 92 positioned around at least a portion of the extension tip 90 (i.e., extension tip 90 may extend out past collar portion 92). The collar portion 92 may be configured to engage the female connection 88 of the needle-free connector 56 via a twist-turn or threading engagement, with one or more threads 94 (FIGS. 4-7) formed on an interior surface of the collar portion 92 mating with threads 96 on the female connection 88 of needle-free connector 56.

In some embodiments, the second coupler 82 of connector 58 is also configured as a male connection (hereafter "second male connection 82"), such as a male luer connection, configured to couple with a corresponding female luer connection of a needle-free connector coupled thereto, although it is recognized that second coupler 82 could be a connection of another suitable type (e.g. a female connection). In the catheter system of FIG. 1, the second male connection 82 may thus connect to a female luer connection 98 of needle-free connector 24, which as stated above may be a SmartSite™ needle-free connector from Becton, Dickinson and Co. The second male connection 82 generally includes an extension tip 100 and a collar portion 102, with the collar portion 102 positioned around at least a portion of the extension tip 100 (i.e., extension tip 100 may extend out past collar portion 102). The collar portion 102 may be configured to engage the female connection 98 of the needle-free connector 24 via a twist-turn or threading engagement, similar to coupling of first male connection 80 with female connection 88.

As shown in FIGS. 2-8 regarding the first male connection 80, the collar portion 92 of first male connection 80 is composed of an arrangement of flexible fingers 104 configured to selectively disengage the connector 58 from the needle-free connector 56 to which it is coupled when a force equal to or greater than a pre-determined pulling force is applied between the connector 58 and the needle-free connector 56. In some embodiments, the collar portion 92 includes two (2) flexible fingers 104 (e.g., top and bottom fingers) that are separated from one another, such that each of the fingers 104 is allowed to flex radially outward when a pulling force is applied to the connector 58, with the fingers having the threads 94 formed thereon. Accordingly, when a force equal to or greater than a pre-determined pulling force is applied between the connector 58 and the needle-free connector 56, the flexible fingers 104 bend radially outward and the threads 94 thereon skip over the threads 96 of the needle-free connector 56 as the connector 58 and needle-free connector 56 are pulled apart in the lengthwise direction 66, such that the connector 58 is disengaged from the needle-free connector 56 when a pre-determined separation force is applied to the connector 58 or the needle-free connector 56.

As shown in FIGS. 4-7, the connector 58 also includes a valve system 106 and actuator 108 positioned within the outer housing 60. The actuator 108 is configured to interact with valve system 106 to selectively control operation of the valve system 106 and thereby control fluid flow through the connector 58. The actuator 108 is further configured to selectively enable or prohibit connection of a needle-free connector 56 to the first male connection 80 of the connector 58, to provide a safety feature on the connector 58 by controlling access to or usage of the connector 58.

The actuator 108 of connector 58 is comprised generally of a central platform or base 110, a first protrusion 112, a second protrusion 114, engagement arms 116, and locking fingers 118. The base 110 may be configured to generally match the cross-sectional shape of the housing 60, and may thus have a circular shape or cross-section, in some embodiments. The base 110 may be generally centrally located in the lengthwise direction 66 on actuator 108, and the first protrusion 112 and second protrusion 114 extend outwardly therefrom in opposing directions—with the first protrusion

Figure 5:
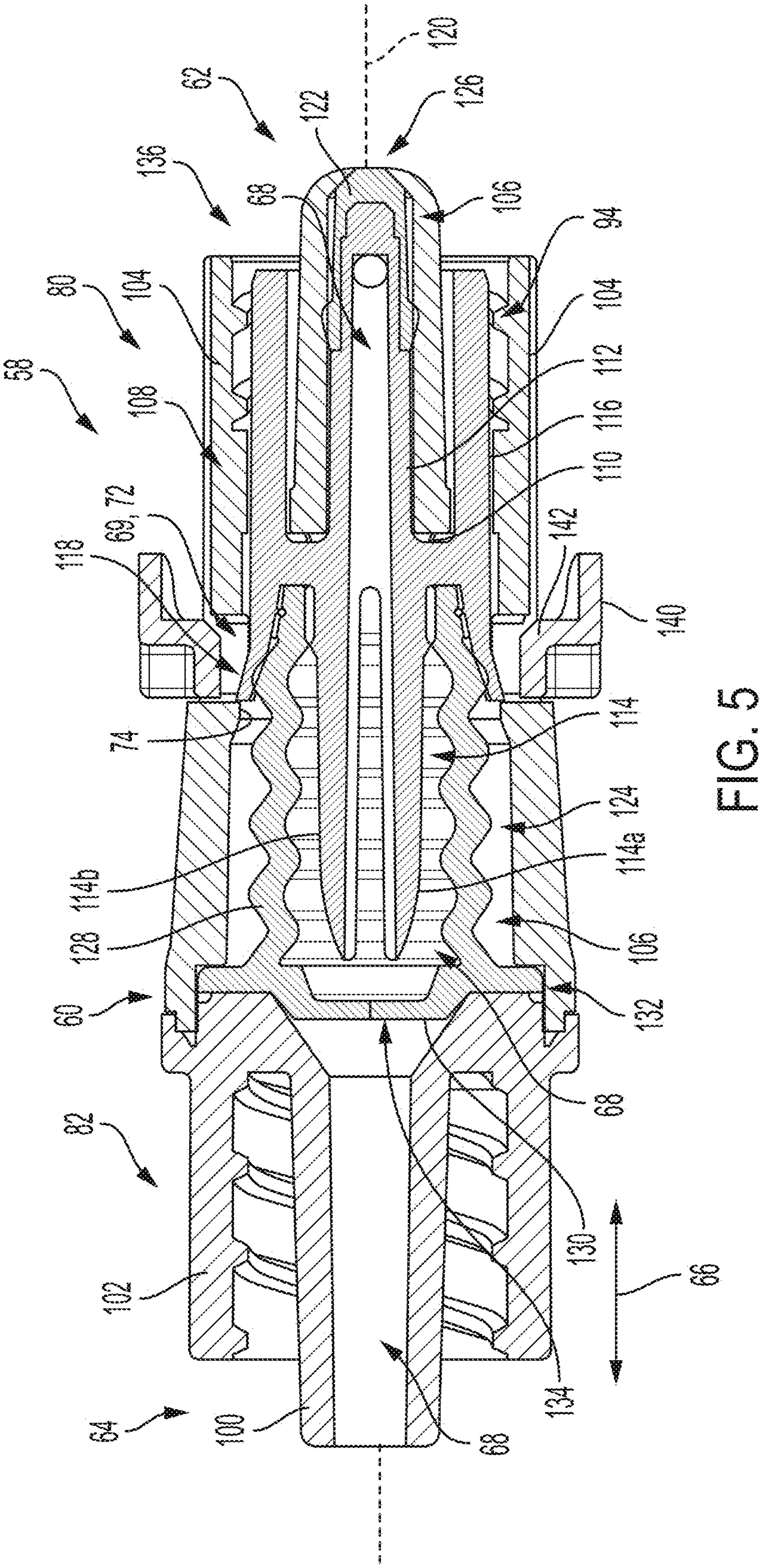
FIG. 5 is a cross-sectional view of the force-controlled release connector of FIG. 2 taken along line 2-2, with the connector in a first configuration.
Figure 7:
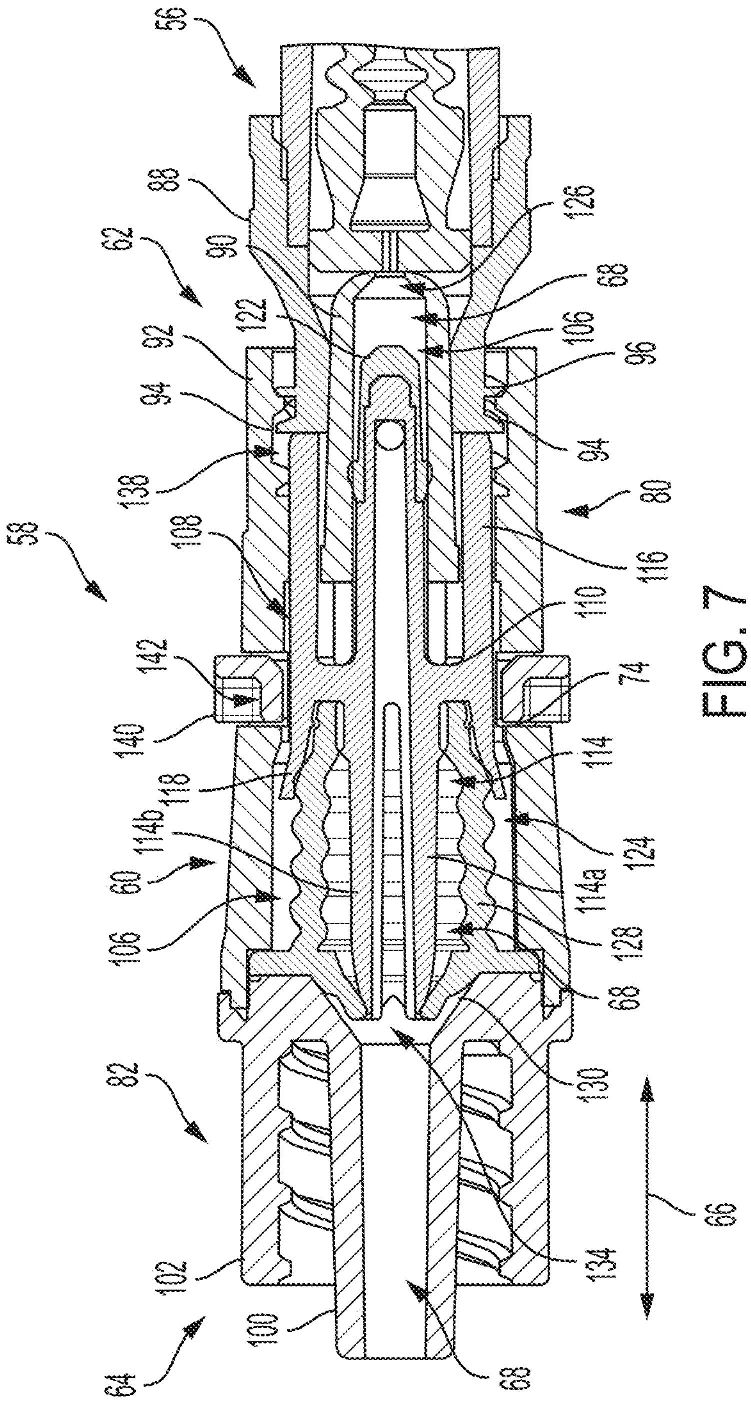
FIG. 7 is a cross-sectional view of the force-controlled release connector of FIG. 2 taken along line 2-2, with the connector in a second configuration.

112 extending out toward the first end 62 of housing 60 and the second protrusion 114 extending out toward the second end 64 of housing 60. Each of the first and second protrusions 112, 114 is centered on base 110, along a centerline 120 of connector 58. The first protrusion 112 is formed such that it is positioned within the extension tip 90 of first male connection 80. More specifically, the first protrusion 112 is formed within a portion of the lumen 68 that extends through the extension tip 90. In some embodiments, the second protrusion 114 is formed as a pair of protrusion fingers 114*a*, 114*b* spaced apart from one another, such as by being vertically spaced apart (as shown in FIGS. 5 and 7) or alternatively being horizontally spaced apart.

Similar to first protrusion 112, the engagement arms 116 of actuator 108 extend outwardly from the base 110 in the lengthwise direction 66, toward the first end 62 of the outer housing 60. In some embodiments, a pair of engagement arms 116 are provided on actuator 108, although it is recognized that a greater number of engagement arms 116 could be included on actuator 108. The engagement arms 116 may have a curved profile that generally matches that of the flexible fingers 104 of outer housing 60, with the profile of the engagement arms 116 allowing for positioned thereof within a radial gap located between the extension tip 90 and the collar portion 92 of first male connection 80. With the engagement arms 116 extending toward the first end 62 of the outer housing 60 and positioned between the extension tip 90 and the collar portion 92 of first male connection 80, the engagement arms 116 are positioned to prohibit mating of a female connection 88 of a needle-free connector with the first male connection 80 and to make contact with the female connection 88 of a needle-free connector 56 when the needle-free connecter 56 is allowed to couple with the connector 58, as will be explained further below.

Regarding the locking fingers 118 of actuator 108, a pair of locking fingers 118 is provided that is configured to extend outwardly from the base 110 in the lengthwise direction 66, toward the second end 64 of the outer housing 60. The locking fingers 118 are provided on opposing edges of the base 110 and are aligned circumferentially with the openings 72 provided in the seat 69 of housing 60. As will be explained in further detail below, the locking fingers 118 may be deflected in the radial direction between a locked position and a movement position, whereby the locking fingers 118 may selectively engage the ledge 74 formed on the inner surface 75 of housing 60, so as to allow or prohibit lengthwise movement of the actuator 108 within the housing 60 between a first position and a second position.

As indicated above, the actuator 108 is configured to interact with valve system 106 to selectively control operation of the valve system 106 and thereby control fluid flow through the connector 58. According to embodiments of the disclosure, the valve system 106 includes two separate valve members-a first valve member 122 and a second valve member 124. The first valve member 122 and the second valve member 124 may function to close off the lumen 68 at two separate locations within connector 58 and, when both closed, may seal off the lumen 68 at generally opposing ends thereof to trap any fluid contained within the lumen 68. Thus, in the embodiment of FIG. 1 for example, IV fluid 44 provided to the connector 58 from IV fluid system 40 may be sealed within the lumen 68 by the valve system 106, upon disconnecting of the needle-free connector 56 from the first male connection 80.

According to embodiments of the disclosure, the first valve member 122 is provided as a plug (hereafter "plug 122") that is positionable to selectively block a first end opening 126 of the lumen 68 in connector 58. The plug 122 is positioned as a cap on an end of first protrusion 112 of actuator 108, such that the plug 122 is positioned within the extension tip 90 of first male connection 80. With the plug 122 positioned on first protrusion 112, the plug 122 is configured to move along with the actuator 108 when the actuator 108 is moved relative to the housing 60.

According to embodiments of the disclosure, the second valve member 124 is configured as a generally cylindrically shaped member that is positioned within housing 60 so as to be retained between the second end 64 of the housing 60 and the base 110 of the actuator 108. The second valve member 124 generally includes a tubular body 128 and a split septum 130. The tubular body 128 is positioned to engage or abut the base 110 at a first end thereof, with the first end of the tubular body 128 retained between the second protrusion 114 and locking fingers 118. The tubular body 128 is sized (i.e., has a diameter) and positioned such that the second protrusion 114 of actuator 108 is arranged within an interior volume of the tubular body 128, while the locking fingers 118 are positioned outside the interior volume, but adjacent an outer surface of the tubular body 128. The split septum 130 is positioned at a second end of the tubular body 128 and, in some embodiments, is secured within the housing 60 by fitting into a notch 132 formed between the first housing portion 84 and the second housing portion 86. Each of the tubular body 128 and split septum 130 is formed of a compliant/resilient material (e.g., an elastomeric material), such that the second valve member 124 is deformable responsive to movement of the actuator 108—with the tubular body 128 being compressed or relaxed in the lengthwise direction 66 responsive to movement of the actuator 108, and a slit 134 of the split septum 130 opening or closing responsive to movement of the actuator 108.

Figure 4:
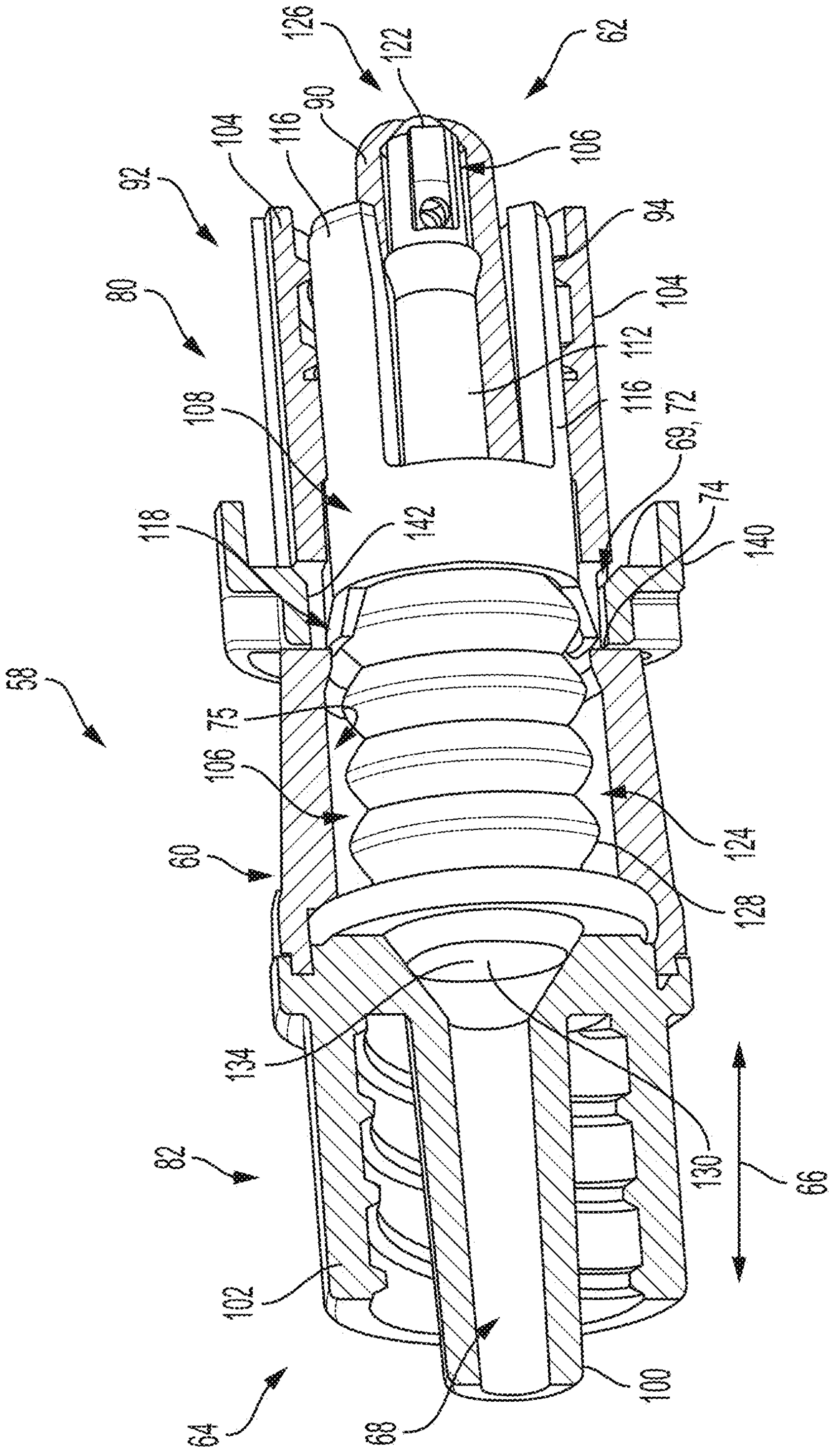
FIG. 4 is a perspective view of the force-controlled release connector of FIG. 2, with a portion of the outer housing removed, and with the connector in a first configuration.
Figure 6:
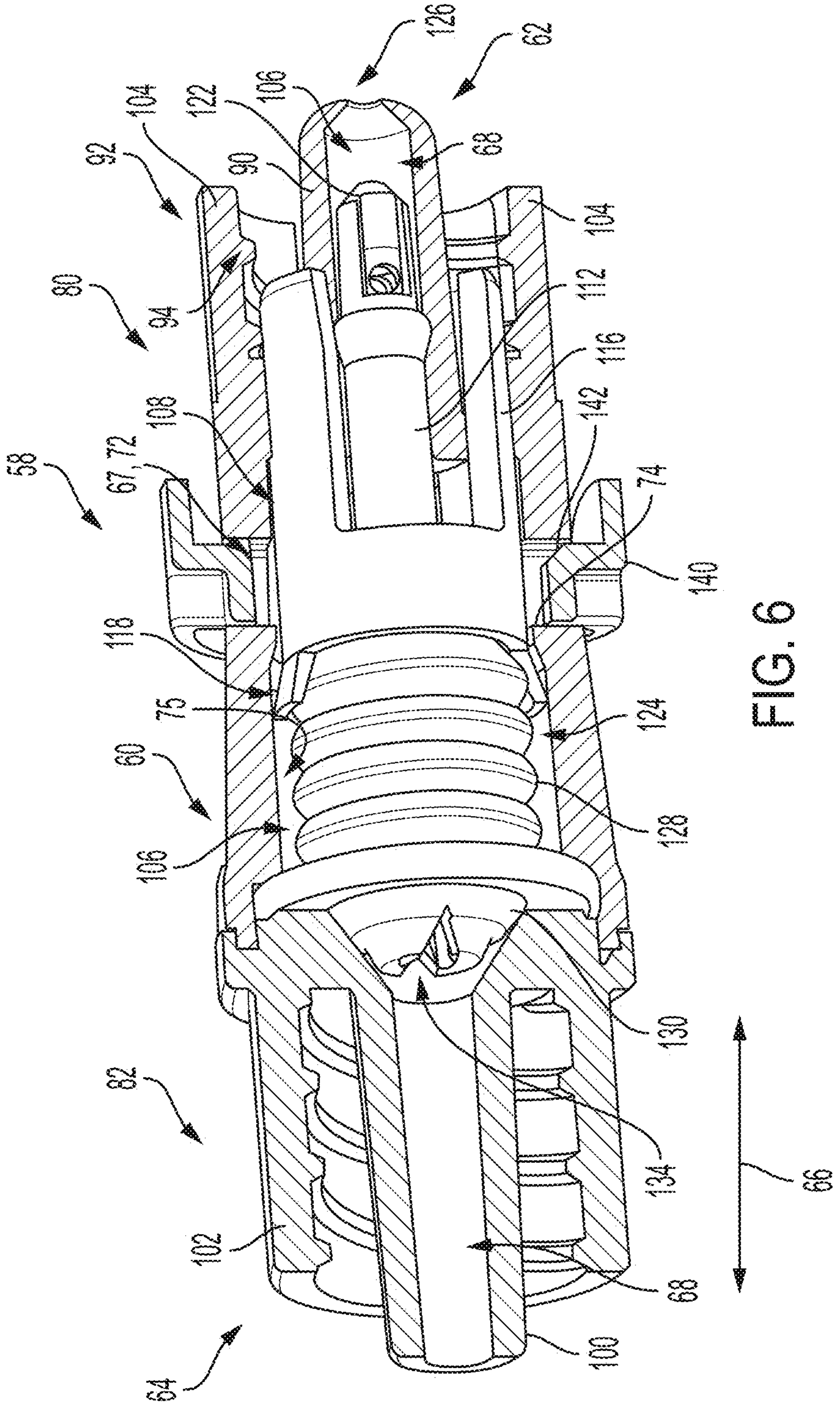
FIG. 6 is a perspective view of the force-controlled release connector of FIG. 2, with a portion of the outer housing removed, and with the connector in a second configuration.

According to embodiments of the disclosure, the actuator 108 is movable lengthwise within the housing 60 between a first position 136 (FIGS. 4 and 5) and a second position 138 (FIGS. 6 and 7). Movement of the actuator 108 between the first position 136 and the second position 138 selectively controls operation/positioning of the first and second valve members 122, 124 and, additionally, controls the ability to connect a needle-free connector 56 to the first male connection 80 of the connector 58. As shown in FIGS. 4 and 5, with the actuator 108 in the first position 136, the plug 122 and the split septum 130 of the valve system 106 are positioned/configured to seal the lumen 68 from the external environment, with the plug 122 blocking the first end opening 126 of the lumen 68 at the end of the extension tip 90 and the split septum 130 being closed shut (i.e., slit 134 is closed) due to the second protrusion 114 of actuator 108 being spaced apart therefrom. As shown in FIGS. 6 and 7, with the actuator 108 in the second position 138, the plug 122 and the split septum 130 of the valve system 106 are positioned/configured such that the lumen 68 is open to the external environment, with the plug 122 being spaced apart from the first end opening 126 of the lumen 68 at the end of the extension tip 90 and the split septum 130 being open (i.e., slit 134 is open) due to the second protrusion 114 contacting and engaging the split septum 130 to force the slit 134 of split septum 130 into the open position (i.e., the pair of protrusion fingers 114*a*, 114*b* of second protrusion 114 make contact on opposing sides of the slit 134 in the split septum 130, to open the slit 134).

As first shown in FIGS. 4 and 5, the connector 58 is initially in a first configuration, where the actuator 108 is at the first position 136 in the lengthwise direction 66 within housing 60. The first configuration is present prior to coupling of a needle-free connector 56 to the first male connection 80 (and subsequent to disconnection of the needle-free connector 56, as will be explained in more detail below). The connector 58 is maintained in the first configuration, and the actuator 108 is retained in the first position 136, via the interaction of locking fingers 118 of actuator 108 with housing 60. That is, the locking fingers 118 are initially in their locked position, where they engage the ledge 74 formed on the inner surface 75 of housing 60 and prevent movement of the actuator 108 in the lengthwise direction 66 from the first position 136 to the second position 138. With the actuator 108 held in the first position 136, the engagement arms 116 of the actuator 108 are positioned adjacent the first end 62 of the housing 60, so as to be almost flush with the end of the collar portion 92 of first male connection 80. The engagement arms 116 thus block access to the first male connection 80 and prevent mating of a female connection (e.g., a female luer connection 88 of needle-free connector 56) with the first male connection 80 of connector 58. Additionally, and as indicated above, with the actuator 108 held in the first position 136, the plug 122 and the split septum 130 of the valve system 106 are positioned/configured to seal the lumen 68 from the external environment, with the plug 122 blocking the first end opening 126 of the lumen 68 and the split septum 130 being closed shut due to the second protrusion 114 of actuator 108 being spaced apart therefrom.

Referring now to FIGS. 6 and 7, the connector 58 is shown as being actuated from the first configuration now to a second configuration, where the actuator 108 is at the second position 138 in the lengthwise direction 66 within housing 60. The second configuration is present upon a needle-free connector 56 being connected to the first male connection 80. The connector 58 is actuated to the second configuration, and the actuator 108 moved to the second position 138, responsive to a two-step actuation process. As a first step of the actuation process, the locking fingers 118 are deflected from their locked position to their movement position. That is, the locking fingers 118 are deflected radially inward, such that they disengage from the ledge 74 on the inner surface 75 of housing 60, with this inwardly deflected position being the movement position. With the locking fingers 118 deflected to their movement position, the actuator 108 is enabled to move in the lengthwise direction 66 from the first position 136 to the second position 138. Movement of the actuator 108 from the first position 136 to the second position 138 is then accomplished via a second step of the actuation process—with the first male connection 80 of connector 58 being introduced into a female connection (e.g., a female luer connection 88 of needle-free connector 56). Insertion of the first male connection 80 of connector 58 into a female connection 88 causes the engagement arms 116 of actuator 108 to contact the female connection 88, thereby pushing the actuator 108 toward the second end 64 of housing 60 and causing the actuator 108 to translate from the first position 136 to the second position 138. As indicated above, with the actuator 108 moved to the second position 138, the plug 122 and the split septum 130 of the valve system 106 are positioned/configured such that the lumen 68 is open to the external environment, with the plug 122 being spaced apart from the first end opening 126 of the lumen 68 and the split septum 130 being open due to the second protrusion 114 (i.e., the protrusion fingers 114*a*, 114*b* of second protrusion 114) contacting and engaging the split septum 130 to force the split septum 130 into the open position.

According to embodiments of the disclosure, the first step of the actuation process as described above—where the locking fingers 118 are deflected from their locked position to their movement position—is performed via a pinch clamp 140 included in connector 58. The pinch clamp 140 is engageable with the locking fingers 118 of actuator 108 to deflect the locking fingers 118 from their locked position to their movement position, thereby enabling movement of the actuator 108 from the first position 136 to the second position 138. As shown in the embodiment of FIGS. 2-7, the pinch clamp 140 may be configured as a pinch collar (hereafter "pinch collar 140") that is positioned about the housing 60 and within the seat 69 formed therein. The pinch collar 140 is annular in shape and includes a pair of protrusions 142 formed on an inner surface thereof. The protrusions 142 on pinch collar 140 may be circumferentially aligned with the openings 72 formed in seat 69, such that the protrusions 142 are positioned within the openings 72. The pinch collar 140 is formed of a flexible material (e.g., a polymeric material) that allows for the pinch collar 140 to be deformed responsive to a pinching force being applied thereto by a clinician. The pinch collar 140 may thus be compressed/pinched by a clinician so as to cause the protrusions 142 of the pinch collar 140 to deflect radially inward, down through the openings 72 in housing 60, and into contact with the locking fingers 118 of actuator 108. The protrusions 142 may thus cause the locking fingers 118 to deflect radially inward from their locked position to their movement position, thereby enabling the actuator 108 to be moved from its first position 136 to its second position 138 and the connector 58 to change from the first configuration to the second configuration. In some embodiments, actuation of the connector 58 from the first configuration to the second configuration is only enabled via use of the pinch collar 140 and the deflection of locking fingers 118 provided thereby, as access to the locking fingers 118 by other means is otherwise prevented (e.g., the openings 72 in housing 60 are too small to allow fingers to manually depress or deflect the locking fingers 118).

In some embodiments, the pinch collar 140 may be configured to be removable from the connector 58 after an initial actuation of the connector 58 from the first configuration to the second configuration has been performed—i.e., with a needle-free connector 56 coupled to the first male connection 80 of connector 58. The pinch collar 140 may be removed from the outer housing 60 by a clinician via any of a number of suitable means. In one embodiment, the pinch collar 140 may be slid off of the outer housing 60 by urging the pinch collar 140 out of the seat 69 of housing 60 and then sliding the protrusions 142 of the pinch collar 140 along and within the pair of channels 76 formed in the housing 60, such that the pinch collar 140 may be slid off past the first end 62 of the housing 60. In another embodiment, the pinch collar 140 may have a break formed therein (not shown) rather than being a continuous ring-shaped member—with the break in the pinch collar 140 and the flexible nature of the pinch collar 140 allowing the pinch collar 140 to be separated at the break and removed from the outer housing 60.

Figure 8:
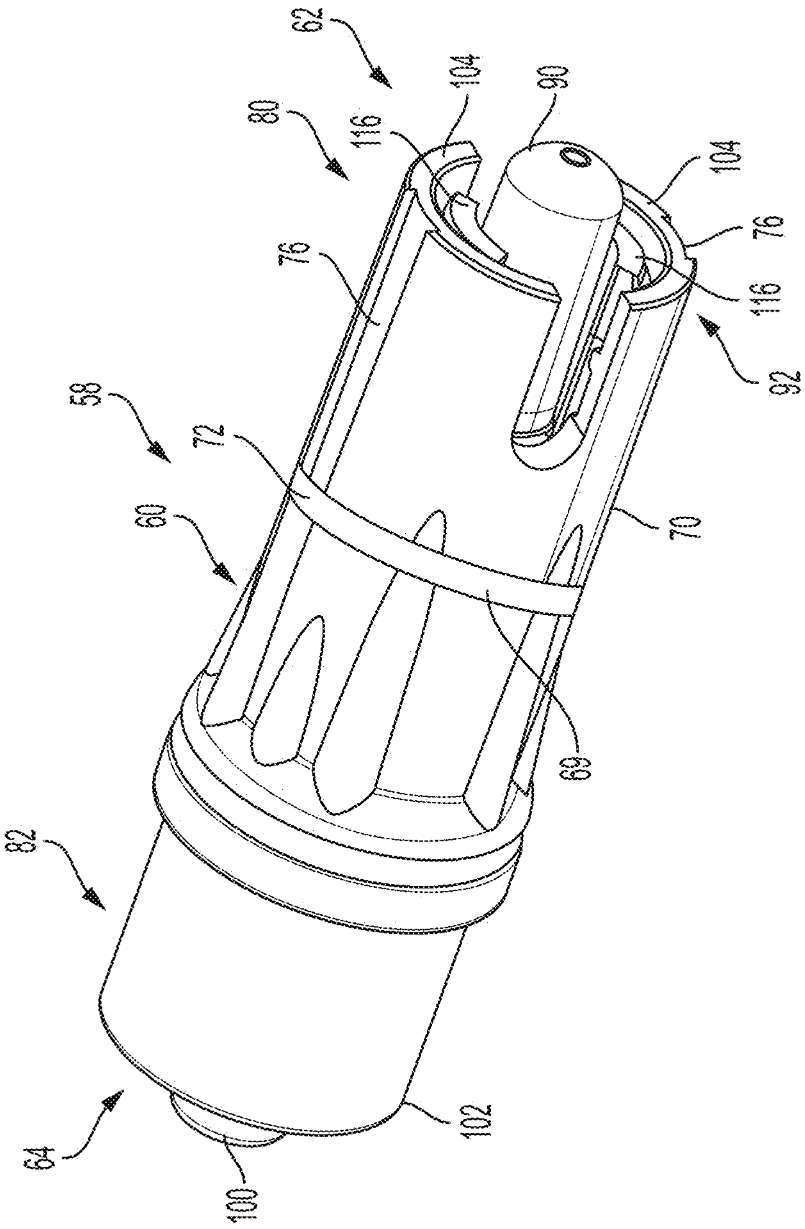
FIG. 8 is a perspective view of the force-controlled release connector of FIG. 2, with a pinch collar removed therefrom, and with the connector in a first configuration.

With the pinch collar 140 removed from the connector 58, the connector 58 is prevented from subsequently being actuated again back into the second configuration. That is, in the event of the first male connection 80 of connector 58 being disconnected from the needle-free connector 56—such as when a separating pulling force is applied between the connector 58 and the needle-free connector 56 coupled to the first male connection 80 thereof that is greater than the predetermined pulling force of the force-controlled release connector 58—the connector 58 is configured to prohibit reattachment of the needle-free connector 56. According to embodiments of the disclosure, and as shown in FIG. 8, the connector 58 is automatically returned to the first configuration (i.e., the actuator 108 is returned to the first position 136) upon the needle-free connector 56 becoming disconnected from the first male connection 80 of connector 58. In one embodiment, the tubular body 128 of second valve member 124 (FIGS. 4-7) is configured to apply a spring-like force that biases the actuator 108 back to the first position 136, upon disconnection of the needle-free connector 56. With the pinch collar 140 removed from the connector 58 and the connector 58 in the first configuration, access to the connector 58 is prohibited and there is no means by which an unauthorized user (e.g., a patient) can actuate the connector 58 from the first configuration to the second configuration. That is, as indicated previously, actuation of the connector 58 from the first configuration to the second configuration is only enabled via use of the pinch collar 140 and the deflection of locking fingers 118 provided thereby, as access to the locking fingers 118 by other means is otherwise prevented. Thus, with pinch collar 140 removed from connector 58, the connector 58 is inaccessible and cannot be actuated from the first configuration to the second configuration. Accordingly, the connector 58 is envisioned as a single-use connector that is to be discarded after disconnection of the needle-free connector(s) therefrom.

Beneficially, embodiments of the disclosure provide a force-controlled release connector for coupling to needle-free connectors, such as may be used in a catheter system for administering fluids to a patient via an in-dwelling catheter. The force-controlled release connector is configured to disconnect from a needle-free connector coupled thereto, so as to prevent pulling forces from being transferred to the in-dwelling catheter that may cause dislodgement thereof. The force-controlled release connector is further configured as a single-use, disposable connector that prevents an unauthorized reconnection of a needle-free connector thereto. The force-controlled release connector is still further configured prevent fluid leakage from within the connector upon disconnection of needle-free connector therefrom, with a valve system within the connector sealing-off an interior volume of the connector, and any fluid therein, upon a disconnection of the needle-free connector.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A force-controlled release connector coupleable to a needle-free valve, the connector comprising:
- an outer housing comprising a first end and a second end, the outer housing defining a lumen extending between the first end and the second end;
- a first coupler positioned at the first end of the outer housing, the first coupler comprising a first male connection mateable with a female connection of the needle-free valve and being separable from the needle-free valve when a pre-determined pulling force is applied between the first male connection and the needle-free valve;
- a second coupler positioned at the second end of the outer housing;
- a valve system positioned within the outer housing to control fluid flow through the lumen; and
- an actuator movable within the outer housing in a lengthwise direction between a first position and a second position;
- wherein the actuator, when in the first position, causes the valve system to be in a closed state that seals the lumen from an external environment and blocks the first coupler from coupling with the needle-free valve; and
- wherein the actuator, when in the second position, causes the valve system to be in an open state that opens the lumen to the external environment and allows the first coupler to couple with the needle-free valve and coupling.

2. The connector of claim 1, wherein the first male connection comprises:
- an extension tip; and
- a collar portion positioned about at least a portion of the extension tip, the collar portion having an arrangement of flexible fingers configured to selectively disengage the connector from the needle-free valve when the pre-determined pulling force is applied.

3. The connector of claim 2, wherein the actuator comprises:
- a base;
- a first protrusion extending outwardly from the base toward the first end of the outer housing, the first protrusion positioned within a portion of the lumen that extends through the extension tip;
- a second protrusion extending outwardly from the base toward the second end of the outer housing; and
- engagement arms extending outwardly from the base toward the first end of the outer housing, the engagement arms positioned partially about the extension tip and positioned to engage the needle-free valve.

4. The connector of claim 3, wherein valve system comprises:
- a first valve member comprising a plug positioned on an end of the first protrusion; and
- a second valve member retained within the housing between the second end of the housing and the base of the actuator, the second valve member comprising a tubular body that engages the base at a first end of the tubular body, with a split septum positioned at a second end of the tubular body.

5. The connector of claim 4, wherein the tubular body biases the actuator in the first position, with engaging of the needle-free valve with the first coupler moving the actuator from the first position to the second position and disengaging of the needle-free valve from the first coupler returning the actuator to the first position.

6. The connector of claim 4, wherein with the actuator in the first position, the plug blocks a first end opening of the lumen positioned at an end of the extension tip, and the second protrusion is spaced apart from the split septum and the split septum is in a closed position, such that the first valve member and the second valve member seal the lumen from the external environment.

7. The connector of claim 6, wherein with the actuator in the second position, the plug is spaced apart from the first end opening of the lumen positioned at the end of the extension tip, and the second protrusion contacts and engages the split septum to force the split septum into an open position, such that the first valve member and the second valve member open the lumen to the external environment.

8. The connector of claim 7, wherein the second protrusion comprises a pair of protrusion fingers spaced apart to make contact on opposing sides of a slit in the split septum.

9. The connector of claim 1, wherein the second coupler comprises a second male connection including another extension tip and another collar portion, the second male connection mateable with a female connection of another needle-free valve.

10. The connector of claim 9, wherein the outer housing comprises a first housing portion and a second housing portion, wherein the first housing portion comprises the first coupler and the second housing portion comprises the second coupler.

11. A catheter system comprising:

a catheter having a catheter distal end and a catheter proximal end;

a catheter adapter coupled to the catheter proximal end and including a lumen in fluid communication with the catheter, the catheter adapter including a side port in fluid communication with the lumen;

an extension tubing in fluid communication with the side port of the catheter adapter, the extension tubing having a proximal access port coupled to a proximal end portion thereof; and a connector, comprising:

an outer housing comprising a first end and a second end, the outer housing defining a lumen extending between the first end and the second end;

a first coupler positioned at the first end of the outer housing, the first coupler comprising a first male connection mateable with a female connection of a needle-free valve and being separable from the needle-free valve when a pre-determined pulling force is applied between the first male connection and the needle-free valve;

a second coupler positioned at the second end of the outer housing;

a valve system positioned within the outer housing to control fluid flow through the lumen; and an actuator movable within the outer housing in a lengthwise direction between a first position and a second position;

wherein the actuator, when in the first position, causes the valve system to be in a closed state that seals the lumen from an external environment and blocks the first coupler from coupling with the needle-free valve; and wherein the actuator, when in the second position, causes the valve system to be in an open state that opens the lumen to the external environment and allows the first coupler to couple with the needle-free valve and coupling; and wherein the second coupler of the connector is coupled to the proximal access port.

12. The catheter system of claim 11, further comprising:

an intravenous (IV) fluid system comprising an IV bag having IV fluid therein and IV tubing extending out from the IV bag;

wherein the needle-free valve is coupled to an end of the IV tubing opposite the IV bag; and wherein the needle-free valve is coupled to the first male connection of the connector.

13. The catheter system of claim 12, wherein an arrangement of flexible fingers of the first male connection is configured to selectively disengage the connector from the needle-free valve when the pre-determined pulling force is applied to the needle-free valve, via the IV tubing.

14. The catheter system of claim 11, wherein the proximal access port comprises another needle-free valve, the another needle-free valve coupled to a second male connection of the second coupler.

* * * * *